(12) United States Patent
Lee

(10) Patent No.: US 6,787,625 B2
(45) Date of Patent: Sep. 7, 2004

US006787625B2

(54) POLYORGANOSILSESQUIOXANE AND PROCESS FOR PREPARING THE SAME

(75) Inventor: Eung-Chan Lee, Seoul (KR)

(73) Assignee: Intersilicone Ltd. (KR)

( * ) Notice: Subject to any disclaimer, the term of this patent is extended or adjusted under 35 U.S.C. 154(b) by 0 days.

(21) Appl. No.: 10/204,226

(22) PCT Filed: Feb. 17, 2001

(86) PCT No.: PCT/KR01/00237
§ 371 (c)(1),
(2), (4) Date: Aug. 19, 2002

(87) PCT Pub. No.: WO01/60880
PCT Pub. Date: Aug. 23, 2001

(65) Prior Publication Data
US 2003/0055195 A1 Mar. 20, 2003

(30) Foreign Application Priority Data
Feb. 17, 2000 (KR) .......................................... 2000-7549

(51) Int. Cl.[7] ........................ C08G 77/06; C08G 77/04; C07F 7/02; C07F 7/21
(52) U.S. Cl. ......................... 528/33; 556/450; 556/451; 556/452; 556/460; 556/462
(58) Field of Search .............................. 528/12, 20, 21, 528/33; 556/450, 451, 452, 460, 462

(56) References Cited

U.S. PATENT DOCUMENTS

| | | | | |
|---|---|---|---|---|
| 4,600,685 A | * | 7/1986 | Kitakohji et al. | 430/313 |
| 4,670,299 A | * | 6/1987 | Fukuyama et al. | 427/96 |
| 4,722,881 A | * | 2/1988 | Ueno et al. | 430/192 |
| 4,962,156 A | * | 10/1990 | Shinjo et al. | 525/100 |
| 5,030,699 A | * | 7/1991 | Motoyama et al. | 525/477 |
| 5,039,771 A | * | 8/1991 | Morimoto et al. | 528/14 |
| 5,079,299 A | * | 1/1992 | Hisamoto et al. | 525/100 |
| 5,179,185 A | * | 1/1993 | Yamamoto et al. | 528/32 |
| 5,399,648 A | * | 3/1995 | Yamamoto et al. | 528/12 |
| 6,251,486 B1 | * | 6/2001 | Chandross et al. | 427/387 |
| 6,340,735 B1 | * | 1/2002 | Yagihashi | 528/37 |
| 2002/0169269 A1 | * | 11/2002 | Hwang et al. | 528/10 |

FOREIGN PATENT DOCUMENTS

| | | | | |
|---|---|---|---|---|
| EP | 242855 A2 | * | 10/1987 | A61K/7/48 |
| JP | 54-072300 A | | 6/1979 | |
| JP | 60-013813 A | | 1/1985 | |
| JP | 61-108628 A | | 5/1986 | |
| JP | 05-039215 A | | 2/1993 | |
| JP | 05-055201 A | | 3/1993 | |
| JP | 07-331050 A | | 12/1995 | |
| JP | 08-059331 A | | 3/1996 | |
| JP | 09-070641 A | | 3/1997 | |
| JP | 10-130393 A | | 5/1998 | |
| JP | 10-161315 A | | 6/1998 | |
| JP | 11-060733 A | | 3/1999 | |

OTHER PUBLICATIONS

Machine translation of JP 07–331050 from JPO website, Osugi et al. Dec. 1995.*
Machine translation of JP 08–059331 from JPO website, Nagata et al. 13–1996.*
Machine translation of JP 09–070641 from JPO website, Sakamoto et al. Mar. 1997.*
Machine translation of JP 11–060733 from JPO website, Osugi et al. Mar. 1999.*
Sugahara et al. "29Si NMR study on co–hydrolysis processes in Si(OEt)4–RSi(OEt)3–EtOH–water–HCl systems (R=Me,Ph): effe of R groups" J. Mater Chem., 1997, 7(1), 53–59.*
Masafumi Unno, et al., "Synthesis, Structure And Reaction Of The Tetrahydroxycyclotetrasiloxane . . . ", Chemistry Letter, 1998, pp. 489–490.
Masafumi Unno, et al., "Formation Of Supermolecule By Assembling Of Two Different Silanols", Chemistry Letter 2000, (3), pp. 242–243.
Masafumi Unno, et al., "Synthesis Of Ladder And Cage Silsesquioxanes From 1,2,3,4–Tetrahydroxycyclotetrasiloxane", Bull. Chem. Soc. Jpn., 73(1), 215–220 (2000).

* cited by examiner

Primary Examiner—Jeffrey B. Robertson
(74) Attorney, Agent, or Firm—Rothwell, Figg, Ernst and Manbeck, P.C.

(57) ABSTRACT

Provided are polyorganosilsesquioxane and process for preparing the same. The polyorganosilsesquioxane is obtained by various methods including polymerization of 1,3-diorganosiloxane, a precursor that is prepared by using silane compounds as starting materials. The polyorganosilsesquioxane has convenience in handling and controlling the rate of polymerization, and structure of highly regular form, and be imparted high functionality and various characteristics as compared to a conventional polyorganosilsesquioxane.

5 Claims, No Drawings

POLYORGANOSILSESQUIOXANE AND PROCESS FOR PREPARING THE SAME

This application is a national phase entry of international application PCT/KR01/00237 filed on Feb. 17, 2001.

BACKGROUND OF THE INVENTION

1. Field of the Invention

The present invention relates to polyorganosilsesquioxane and a process for preparing the same, and more particularly, to polyorganosilsesquioxane having silane-based compounds as starting materials, and a process for preparing the same.

2. Description of the Related Art

With the development of high-level advanced technology, research into high-performance, multi-functional high-technology materials is being conducted in various fields. In particular, in research into novel polymeric materials, much attention has been paid to novel high-functional organic polymers, e.g., organic polymers having improved heat resistance and glass transition temperature (Tg), and technology of forming organic or inorganic hybrid materials, such as an organic and inorganic hybrid complex.

There are known many existing organic or inorganic hybrid materials. In particular, due to importance of thermal stability between organic polymer and inorganic polymer, keen attention is focused on polyorganosilsesquioxane, which is a high-heat-resistance polymer.

Polyorganosilsesquioxane was first introduced in an article of J. Am. Chem. Soc., 82, 6194 (1960) by Brown et al., and commercialized in trade names of "Glass-resin" and "SST-resin" by Owens Illinois and Gelest. However, polyorganosilsesquioxane is not being put into practical use as industrial material because of difficulties of controlling the polymer structure and adjusting the molecular weight thereof.

A highly regular ladder form of polyorganosilsesquioxane accounts for its improved performance properties. Thus, along with development of novel starting materials that can easily form a perfect ladder-form structure, research into condensation methods thereof has been made in various fields of industry in various ways.

Among known methods of preparing polyprganosilsesquioxane, a representative method is to dehydrate and condense a precursor hydrolyzed product (oligomer), synthesized by hydrolyzing trichlorosilane or trialkoxysilane in the presence of alkali/acidic catalyst, thereby easily obtaining a low-molecular weight polymer (having a number-average molecular weight ($M_n$) of 10,000 to 30,000 and a degree of dispersion ($M_w/M_n$) of 3 to 20.

A conventional method of preparing polyorganosilsesquioxane using trichlorosilane will first be described. Oligomer produced by co-hydrolytic condensation when hydrolyzing trichlorosilane, the oligomer having $M_n$ of 1,000 to 2,000 and a polydispersity index value (PDI) of 2 to 5, has a complicated, diverse structure, compared to silanetriol which is a single structure. In the case of forming high-molecular weight oligomer, a three-dimensional network structure is easily formed by constructural deformity due to the presence of inter-hydroxy group, and the inherent structure of oligomer, having the following disadvantages: 1) The structure of produced polymer is uncontrollable; 2) It is difficult to adjust the molecular weight of produced polymer and to obtain high-molecular weight polymer; 3) The produced polymer loses high regularity, lowering solubility against solvent; and 4) Remaining low-molecular weight components may adversely affect the heat resistance and mechanical property of polymer.

A conventional process for preparing polyorganosilsesquioxane using trialkoxysilane is also advantageous from the viewpoint of handling convenience, such as controllability of a hydrolysis rate, compared to trichlorosilane. However, various studies reported that this process had the following disadvantages caused by the oligomer molecular deformity due to the presence of inter-hydroxy group, and by the presence of alkoxy group: 1) A polymer of a branch structure, rather than a ladder structure, is formed; 2) selection of catalyst used, amount of the selected catalyst, selection of reactant solvent, careful adjustment of pH of selected reactant solvent, and so on, are not easy to achieve; and 3) a three-dimensional network structure causes microgelation. These disadvantages may adversely affect preparation of highly regular silicon ladder-form polymer.

As described above, a great attention has been paid to polyorganosilsesquioxane and constant research into the same has been made.

According to known various synthesizing methods, e.g., a sol-gel method, a ring-opening polymerization method or an equilibrium polymerization method, and research into the structure of polyorganosilsesquioxane, condensation thereof is very complicated and versatile, so that the structure of polymer cannot be sufficiently controlled. Thus, even a product commercially available in the trade name of glass resin, also called T-type resin, cannot meet several requirements to be used as a novel industrial material, which becomes impediment to practical use.

Requirements of novel industrial materials using organic or inorganic hybrid materials are: a low dielectric constant of 2 to 3; excellent thermal stability such as a pyrolysis starting temperature of 400° C. or higher; low hygroscopicity; a low thermal expansion coefficient; excellent gap filling capability; excellent bondability.

To overcome the above-described problems, the present inventors proposed polyphenylsilsesquioxane having high regularity and crystallinity, which cannot be controlled by conventional methods(sol-gel method), using high-purity organosilanetriol as a starting material, rather than oligomer having various molecular weights and structures.

However, there is still a need for polyorganosilsesquioxane having high regularity/crystallinity.

SUMMARY OF THE INVENTION

It is an objective of the present invention to provide a novel high-technology inorganic material having excellent properties through development of new precursors, and preparation method thereof, the precursors being: 1) easy in handling; 2) capable of adjusting the rate of polymerization; 3) capable of uniformly distributing hydroxy groups at both ends of polymer; 4) capable of introducing R—$SiO_{3/2}$ to the main chain of polymer with high regularity; 5) easily capable of adjusting the crosslinking structure of polymer, specifically, crosslinkablity or crosslinking density; 6) capable of facilitating chemical modification by spreading the structure of polymer; 7) easily capable of forming nano-sized pores in the backbone of polymer; and 8) capable of imparting high functionality and versatile properties to polymer.

To accomplish the above objective of the present invention, there is provided polyorganosilsesquioxane and a process for preparing the same.

Polyorganosilsesquioxane according to the present invention is a compound represented by formula 1:

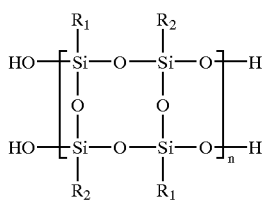

[Formula 1]

1 wherein $R_1$ and $R_2$ are independently a hydrogen atom, an unsubstituted or substituted aliphatic hydrocarbon group having 1 to 30 carbon atoms, an unsubstituted or substituted aromatic hydrocarbon group having 1 to 30 carbon atoms, an unsubstituted or substituted alicyclic hydrocarbon group having 1 to 30 carbon atoms, an unsubstituted or substituted silyl group having 1 to 30 carbon atoms, an unsubstituted or substituted allyl group having 1 to 30 carbon atoms, an unsubstituted or substituted acyl group having 1 to 30 carbon atoms, a vinyl group, an amine group, an acetate group or an alkali metal, and n is an integer of 2 to 300,000.

In the present invention, 1,3-diorganorsiloxane represented by formula 2 is provided as a precursor for preparing the polyorganosilsesquioxane represented by Formula 1:

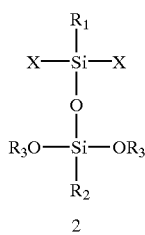

[Formula 2]

2 wherein $R_1$ and $R_2$ are as defined above, $R_3$ is a hydrogen atom, a lower alkyl group, acetate, sodium or potassium, and X represents a hydrogen atom, a halogen atom, a hydroxy group, an amine group or a carboxy group.

The process for preparing the polyorganosilsesquioxane according to the present invention can be expressed in the reaction scheme 1:

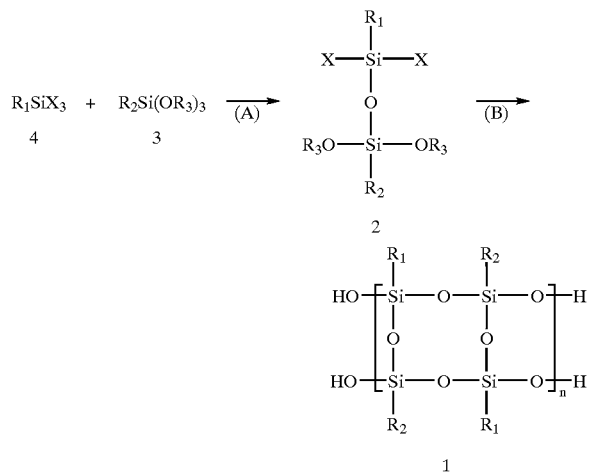

[Reaction Scheme 1]

wherein $R_1$, $R_2$ and $R_3$ are as defined above, and n and X are as defined above.

The step (A) of the reaction scheme 1 is a step for preparing the compound which is a precursor for preparing polyorganosilsesquioxane of the present invention, represented by Formula 1, the precursor represented by Formula 2. In step (A), a compound represented by Formula 4, e.g., trichloromethylsilane, and a compound represented by Formula 3, e.g., trimethoxyphenylsilane, which are used as starting materials, are reacted in the presence of acidic catalyst or without catalyst, thereby easily preparing various kinds of compounds represented by Formula 2.

The organic solvent used in the above reaction is not specifically limited as long as it can be generally used in the art, but THF, benzene, anisol, chlorobenzene, xylene, methylisobutylketone (MIBK), dimethylformamide (DMF), N-methylpyrrolidone (NMP), 1,4-dioxane, dimethylacetamicle (DMAC), acetone, or toluene is preferably used.

As the catalyst used in the above reaction, HCl, acetone, triethylamine, tin, pyridine, trichloroacetic acid or an acetic acid-amine complex catalyst is preferably used, and specifically, trichloroacetic acid is more preferably used from the viewpoint of reaction rate, temperature and yield.

The reaction temperature is preferably 30 to 350° C., and the reaction time is preferably 1 to 300 hours.

The compound represented by Formula 2 obtained as a precursor, is polymeric-condensed in an organic solvent, as represented by the step (B) of the reaction scheme 1 by the conventional method, thereby obtaining the polyorganosilsesquioxane represented by Formula 1.

The polymeric-condensation method used in step (B) of the reaction scheme 1 is not specifically limited, and various methods including heating, light radiation, electron beam scanning, microwave radiation and the like may be used. In the case of adding a catalyst, a compound having a large value of n can be obtained.

The compound used in step (B) of the reaction scheme 1 is preferably in the range of 5 to 300 parts by weight, preferably 10 to 100 parts by weight based on 100 parts by weight of organic solvent. If the amount of the compound represented by Formula 2 is less than 5 parts by weight, the polymeric-condensation may be retarded or the reaction is not fully carried out, and if greater than 300 parts by weight, gelation may undesirably occur during reaction.

The catalyst used for facilitating the polymeric-condensation in step (B) of the reaction scheme 1, is not specifically limited, but at least one material selected from the group consisting of alkali metal hydroxides such as sodium hydroxide, potassium hydroxide or cesium hydroxide, amines such as triethylamine, diethylene triamine, meth-butylamine, para-dimethylamine ethanol, triethanol amine, or quaternary ammonium salts, and fluorides. The catalyst used for polymeric-condensation is preferably in the range of 0.001 to 5 parts by weight, more preferably 0.001 to 1 part by weight based on 100 parts by weight of the compound represented by Formula 2.

In particular, in the case of using alkali metal hydroxide as a catalyst, it is preferred that the compound represented by Formula 2 is hydrolyzed in advance to thus produce a hydrolyzed product and polymeric-condensation is then carried out.

The organic solvent used in step (B) of the reaction scheme 2 is not specifically limited, and an organic solvent having a boiling point of 100° C. or higher, such as toluene or NMP, is preferably used.

In step (B) of the reaction scheme 1, the reaction temperature is preferably 50 to 350° C., more preferably 100 to 200° C. The reaction time is preferably 1 to 50 hours in the case of using a catalyst. In the case of not using any catalyst, the reaction temperature is preferably 150 to 350° C., and the reaction time is preferably 1 to 200 hours. If the reaction temperature is out of this range, the efficiency of the polymeric-condensation cannot meet industrial requirement.

Also, if the purity of the compound represented by Formula 2 for polymeric-condensation, is greater than or equal to 90%, a high molecular weight polymer, that is, $M_n$>500,000, can be obtained by the phase transition method.

The polyorganosilsesquioxane represented by Formula 1 according to the present invention has a high solubility to a general organic solvent, and is soluble in organic solvents including aromatic hydrocarbons such as toluene, xylene, benzene or chlorobenzene, hydrocarbons such as methylene chloride or chloroethane, ethers such as THF, 1,4-dioxane, diethylether or dibutylether, ketones such as acetone, methyethylketone or methyletherketone, esters, or dimethylformamide.

In the present invention, $R_1$ and $R_2$ are independently a hydrogen atom, an unsubstituted or substituted aliphatic hydrocarbon group having 1 to 30 carbon atoms, an unsubstituted or substituted aromatic hydrocarbon group having 1 to 30 carbon atoms, an unsubstituted or substituted alicyclic hydrocarbon group having 1 to 30 carbon atoms, an unsubstituted or substituted silyl group having 1 to 30 carbon atoms, an unsubstituted or substituted allyl group having 1 to 30 carbon atoms, an unsubstituted or substituted acyl group having 1 to 30 carbon atoms, a vinyl group, an amine group, an acetate group or an alkali metal, preferably a lower alkyl such as a hydrogen atom, a methyl group, an ethyl group or a propyl group, a phenyl group, a phenol group, a chlorophenyl group, vinyl group, carboxyl group, a trimethylsilyl group, acetate or alkali metal, and more preferably a hydrogen atom, a methyl group, a vinyl group or a trimethylsilyl.

As described above, according to the present invention, unlike in conventional polyorganosilsesquioxane obtained by heat-condensing oligomer prepared by hydrolyzing conventional trichlorosilane or triethoxysilane, a silane-based compound is first reacted as a starting material to obtain 1,3-diorganosiloxane, which is a precursor, and then polymeric-condensed to obtain polyorganosilsesquioxane, thereby synthesizing a highly-regular ladder-form polymer having repeating units of cyclotetraorganosilsesquioxane.

As described above, since Si—O—Si bonds and ladder-form structures are easily formed in the main chain of polymer with high regularity, high-heat-resistance can be maintained. Also, since inter-hydroxy group structures or defects existing in the main chain of polymer can be reduced, no thermal treatment is required and various functional side chains (e.g., a photosensitive group or dealkyl reactive group) can be introduced. In particular, the physical property of polymer depending on a composition ratio of the introduced side chains, e.g., a difference in the ratio of phenyl to methyl, can be changed, and new polymeric molecules can be designed. Since terminal-silanol groups can be arranged regularly at the terminal of polymer so that the amount of organic polymer introduced can be adjusted in preparing organic or inorganic hybrid materials, thereby easily preparing an organic or inorganic copolymer.

In particular, the polyorganosilsesquioxane prepared according to the present invention has a unique molecular structure, that is, the ratio of siloxane (Si—O—Si) bonds and rigid ladder-form structures (R—SiO$_{3/2}$) present in the main chain of the polyorganosilsesquioxane prepared according to the present invention is 97% more than in the conventional polyorganosilsesquioxane, the percentage being represented by
{No.of R—SiO$_{3/2}$)÷(No.of hydroxygroups+No.of terminal-silanol groups)×100}.

Thus, the polyorganosilsesquioxane prepared according to the present invention exhibits high solubility to a general organic solvent, and has excellent anti-wearability, low surface tension, optical transparency, low dielectric constant of 3.0 or less, low absorption ratio, excellent gap filling capability and so on. Also, the polyorganosilsesquioxane prepared according to the present invention is excellent in view of adhesion to glass or metal, e.g., aluminum, copper, titanium or silicon, electric insulation, water drainage, chemical resistance or transparency, by introducing different side chains, and can be commercially applicable in a wide range of industrial materials.

The polyorganosilsesquioxane prepared according to the present invention can be used in various fields: UV curable resins and silane compounds are widely used; and glass resins are also used in some fields. Materials of the polyorganosilsesquioxane prepared according to the present invention include polycarbonate, acryl resin, diethylglycolbis-alkylcarbonate (in the trade name of "CR-39") and so on. The polyorganosilsesquioxane prepared according to the present invention can be used for plastic, sunglasses, protective glasses, dash board, automobile lamps, aircraft windows or bulletproof glass. Also, the polyorganosilsesquioxane prepared according to the present invention can be used for thermally treating glass lenses with glass resin.

Further, the polyorganosilsesquioxane prepared according to the present invention is excellent in view of electric insulation, heat resistance, low absorption, planarization of a spin-on glass (SOG) solution, thereby being adapted to electronic usage. For example, the polyorganosilsesquioxane prepared according to the present invention is a general-purpose material that can be used as a protective coating for a thin film, an interlayer dielectric film in LSI multiple layer wiring, a low dielectric material, a multiple insulation film, an LCD insulator film and the like.

Recently, as a highly integrated semiconductor device has become narrower in line space, the thickness of formed coating layers unavoidably increase, resulting in cracks. Generation of cracks is presumably caused by the following factors: 1) thermal curing contraction stress generated when inter-hydroxy groups or terminal-silanol groups are mutually condensed; and 2) a difference in thermal stress depending on a difference in the thermal expansion coefficient among a cured film, an aluminum wiring and a silicon wafer. In the present invention, since the presence ratio of inter-hydroxy groups is low due to a defective structure of polymer, that is less than or equal to 5%, a reaction occurring at the terminal can be prevented by introducing silylation or double bond into the terminal-silanol group, and new functionality of an organic-inorganic hybrid material can be attained by introducing other organic polymer, specifically polyimide, polyamide, PMMA, polyacryl, polycarbonate, polystyrene or polyurethane.

Further, the polyorganosilsesquioxane prepared according to the present invention is soluble in various solvents to form a thin film easily and has a high level of hardness of 4 to 8H. Also, since the polyorganosilsesquioxane prepared according to the present invention can form a highly transparent thin film, it can be commercialized together with optically functional organic polymers, thereby increasing the long-term reliability of optical fiber. Also, since the polyorganosilsesquioxane prepared according to the present invention is used as a material for forming a coating on the surface of a resistor, it can be applied for electric/electronic materials.

Also, the polyorganosilsesquioxane prepared according to the present invention can be used as a metal release agent in plastic molding plastic, e.g., urethane reactive injection molding (RIM), or in manufacturing glass. Further, a mixture of RTV and the polyorganosilsesquioxane prepared according to the present invention can be used as a tile adhesive agent or outer surface coating of a space shuttle, a binder of optical fiber, and the like, and can be used for heat-resistive coating materials owing to its heat resistance and corrosion resistance.

The applicability of the final product according to the present invention will be boundlessly extended, not limited to the above-described fields, along with the development of advanced technology.

DETAILED DESCRIPTION OF THE INVENTION

For better understanding of the present invention, the invention will now be described in detail through preferred embodiments with reference to the accompanying drawings. The present invention may, however, be embodied in different forms and should not be construed as limited to the embodiments set forth herein. Rather, those embodiments are provided so that this disclosure will be thorough and complete, and will fully convey the scope of the invention to those skilled in the art.

EXAMPLE 1

Preparation of a Compound Represented by Formula 1; (1,1-dichloromethyl-3,3-diethoxyphenylsiloxane) ($R_1$=methyl, $R_2$=phenyl)

A reflux condenser and a 100 ml dropping funnel were placed in a 500 ml three-necked round bottom flask and dried with flame under a nitrogen atmosphere. 19.8 ml of trimethoxyphenylsilane and 1.6 ml of $CCl_3COOH$ were dissolved in acetone and stirred for 4 hours. Thereafter, 15 ml of trichloromethylsilane was slowly dropped by a dropping funnel and reacted at room temperature for 72 hours. Thereafter, a vacuum distillation device was installed in the reaction system to vacuum-remove unreacted trimethyoxysi lane, trichlorosilane and $CCl_3COOH$, thereby obtaining a white, clear solution (yield: 86%).

$^1$H NMR (500 MHz/CDCl$_3$): δ0.2 (s, Si—Me), 3.5 (s, Si—OMe), 7.2~7.8 (d, Si—Ph) ppm $^{29}$Si NMR (99.3 MHz/CDCl$_3$): δ–7.5 (s, Si—OCH$_3$), –24.8 (s, Si—Cl) ppm GC/Mass spectrometry: $M_n$=296

EXAMPLE 2

Hydrolysis of a Compound Represented by Formula 2; (1,1-dichloromethyl-3,3-diethoxyphenylsiloxane)

A reflux condenser and a 100 ml dropping funnel were placed in a 500 ml three-necked round bottom flask and dried with flame under a nitrogen atmosphere. 30 ml of (1,1-dichloromethyl-3,3-diethoxyphenylsiloxane) prepared in Example 1 was dissolved in 70 ml toluene and then transferred to a dropping funnel. 350 ml of tertiary distilled water and HCl were put into a 500 ml round bottom flask to make the solution pH 2.5, and then 1,1-dichloromethyl-3,3-diethoxyphenylsiloxane was slowly dropped through the dropping funnel to be hydrolyzed at 3° C. After hydrolysis, an organic layer and an aqueous layer were separated using a separating funnel, and the aqueous layer was recrystallized at 3° C. to obtain white, clear powder of hydrolyzed product Ph(OH)$_2$SiOSiMe(OH)$_2$ (yield: 88%).

The white powder was low-temperature dried at 3° C. to be used as an analysis sample.

$^1$H NMR (500 MHz/CDCl$_3$): δ0.8 (s, Si—Me), 2.7~3.25 (s, Si—OH), 7.3~7.78 (d, Si—Ph) ppm; Si—Me/Si—OH/Si—Ph=25.77/23.18/16.36=3/4/5

LC/Mass spectrometry: $M_n$=295.9

EXAMPLE 3

Polymeric-Condensation of Hydrolyzed Product (Ph(OH)$_2$SiOSiMe(OH)$_2$)

A Dean Stark tube was installed in a 50 ml round bottom flask and dried with flame under a nitrogen atmosphere. 10 g of the hydrolyzed product (Ph(OH)$_2$SiOSiMe(OH)$_2$) obtained in Example 2 and 0.1 g of KOH were put into the flask, and 38 ml of toluene was added thereto to dissolve the hydrolyzed product (Ph(OH)$_2$SiOSiMe(OH)$_2$). Subsequently, the resultant was reacted at a reflux temperature of toluene for 18 hours. After reaction, the reactant was dropped to an excess of methanol and agitated for 30 minutes to filter the precipitate, thereby obtaining white powder of a desired product (yield: 98%).

The product was vacuum-dried at 50° C. for 10 hours to be used as an analysis sample.

$^1$H NMR (500 MHz/CDCl$_3$): δ–0.5~0.8 (s, Si—Me), 7.11~7.8 (s, Si—Ph) ppm; 3080~2940 (CH), 1435 (Si—Ph), 1050 (O—Si—Ph), 1150 (O—Si), 750, 700 (Ph)cm$^{-1}$, $^{29}$Si NMR (99.3 MHz/CDCl$_3$): δ–67.7 (Me-T$_3$), –83.7 (Ph-T$_3$) ppm GPC(PST); $M_n$=35,244

Td=480° C.

DC (degree of crosslinking) (%); $T_3/T_{total} \times 100 = 98\%$

Low k=2.72

While the present invention has been described in conjunction with the preferred embodiments, these embodiments are presented for illustrative purposes only, and are not intended as a restriction on the scope of the invention as recited in the appended claims.

What is claimed is:

1. A compound represented by Formula 2:

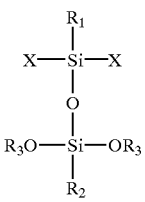

wherein $R_1$ and $R_2$ are different from each other, a hydrogen atom, an unsubstituted or substituted aliphatic hydrocarbon group having 1 to 30 carbon atoms, an unsubstituted or substituted aromatic hydrocarbon group having 1 to 30 carbon atoms, an unsubstituted or substituted alicyclic hydrocarbon group having 1 to 30 carbon atoms, an unsubstituted or substituted silyl group having 1 to 30 carbon atoms, an unsubstituted or substituted allyl group having 1 to 30 carbon atoms, an unsubstituted or substituted acyl group having 1 to 30 carbon atoms, a vinyl group, an amine group, an acetate group or an alkali metal, $R_3$ is a hydrogen atom, a lower alkyl group, acetate, sodium or potassium, and X represents a hydrogen atom, a halogen atom, a hydroxy group, an amine group or a carboxy group.

2. The compound according to claim 1, wherein $R_1$ and $R_2$ are different from each other, and a hydrogen atom, a methyl group, a phenyl group or a trimethylsilyl group, $R_3$ is a hydrogen atom, a methyl group, acetate, sodium or potassium, and X represents a hydrogen atom, chlorine, a hydroxy group, an amine group or a carboxy group.

3. A process for preparing a compound represented by Formula 1 obtained by polymeric-condensing a solution of a compound represented by Formula 2 in an organic solvent:

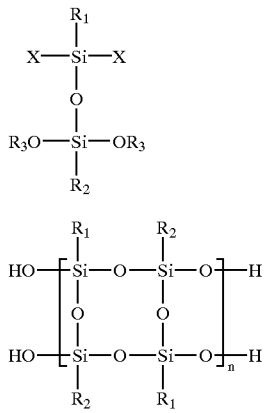

wherein $R_1$ and $R_2$ are independently a hydrogen atom, an unsubstituted or substituted aliphatic hydrocarbon group having 1 to 30 carbon atoms, an unsubstituted or substituted aromatic hydrocarbon group having 1 to 30 carbon atoms, an unsubstituted or substituted alicyclic hydrocarbon group having 1 to 30 carbon atoms, an unsubstituted or substituted silyl group having 1 to 30 carbon atoms, an unsubstituted or substituted allyl group having 1 to 30 carbon atoms, an unsubstituted or substituted acyl group having 1 to 30 carbon atoms, a vinyl group, an amine group, an acetate group or an alkali metal, $R_2$ is a hydrogen atom, a lower alkyl group, acetate, sodium or potassium, X represents a hydrogen atom, a halogen atom, a hydroxy group, an amine group or a carboxy group, n is an integer of 2 to 300,000,
and wherein the polymeric-condensing reaction is one selected from the group consisting of heating, light radiation, microwave radiation and electron beam radiation.

4. A process for preparing a compound represented by Formula 1 obtained by polymeric-condensing a solution of a compound represented by Formula 2 in an organic solvent:

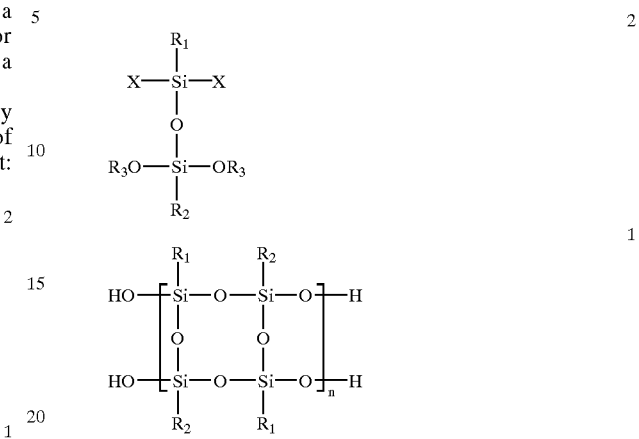

wherein the amount of the compound represented by Formula 2 is 5 to 300 parts by weight based on 100 parts by weight of the organic solvent; and wherein $R_1$, $R_2$, $R_3$, X and n are as defined in claim 3.

5. A process for preparing a compound represented by Formula 2 by reacting a compound represented by Formula 3 and a compound represented by Formula 4:

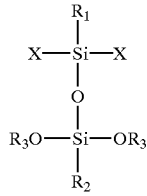

wherein $R_1$, $R_2$ $R_3$ and X are as defined in claim 1 or 2.

* * * * *